US007744862B2

(12) United States Patent
Maglione et al.

(10) Patent No.: US 7,744,862 B2
(45) Date of Patent: *Jun. 29, 2010

(54) PRODUCTION PROCESS OF RECOMBINANT PLACENTAL GROWTH FACTOR

(75) Inventors: Domenico Maglione, Anagni (IT); Mauro Battisti, Carpineto (IT); Ettore Conti, Rocca di Papa (IT); Giuseppe Salvia, Catania (IT); Marina Tucci, Anagni (IT)

(73) Assignee: Geymonat S.p.A., Anagni (IT)

( * ) Notice: Subject to any disclaimer, the term of this patent is extended or adjusted under 35 U.S.C. 154(b) by 1366 days.

This patent is subject to a terminal disclaimer.

(21) Appl. No.: 10/503,911

(22) PCT Filed: Feb. 5, 2002

(86) PCT No.: PCT/IT02/00065

§ 371 (c)(1), (2), (4) Date: Nov. 22, 2004

(87) PCT Pub. No.: WO03/066676

PCT Pub. Date: Aug. 14, 2003

(65) Prior Publication Data

US 2005/0070696 A1 Mar. 31, 2005

(51) Int. Cl.
*A61K 38/18* (2006.01)
*A61K 38/16* (2006.01)
*C12P 21/02* (2006.01)

(52) U.S. Cl. .................. 424/85.1; 424/200.1; 514/2; 514/8; 514/12; 530/399; 530/412; 435/69.1; 435/71.1

(58) Field of Classification Search .................. None
See application file for complete search history.

(56) References Cited

U.S. PATENT DOCUMENTS

| 5,708,148 | A | * | 1/1998 | Schmitz et al. | 530/402 |
| 5,922,846 | A | * | 7/1999 | Cerletti et al. | 530/399 |
| 6,156,517 | A | * | 12/2000 | Mayfield | 435/6 |
| 6,218,181 | B1 | * | 4/2001 | Verma et al. | 435/369 |
| 6,221,608 | B1 | * | 4/2001 | Middleton et al. | 435/7.1 |
| 2002/0119521 | A1 | * | 8/2002 | Palli et al. | 435/69.1 |

FOREIGN PATENT DOCUMENTS

| WO | WO/92/06194 | * | 4/1992 |
| WO | WO/99/61464 | * | 12/1999 |

OTHER PUBLICATIONS

Park et al., Placenta Growth Factor. J. Biol. Chem., 269, 25646-25654, 1994.*
Maglione et al., Recombinant production of PlGF-1 and its activity in animal models, Farmaco, 55, 165-167, 2000.*
Iyer et al., Use of the steric mass action model in ion-exchange chromatographic process development. J. Chromatography A, 832, 1-9, 1999.*
Scrofani et al., Purification and refolding of vascular endothelial growth factor-B. Protein Science, 9, 2018-2025, 2000.*
Li Min et al. Production of Human Recombinant Bone Morphogenetic Protein-2A by High Density Culture of *Escherichia coli* with Stationary Dissolved Oxygen Fed-Batch Contition, Chinese J. of Biotechnology 1999, vol. 14, No. 3, pp. 157-163.

* cited by examiner

*Primary Examiner*—Christine J Saoud
*Assistant Examiner*—Elly-Gerald Stoica
(74) *Attorney, Agent, or Firm*—Timothy H. Van Dyke; Beusse Wolter Sanks Mora & Maire

(57) ABSTRACT

Process for extracting and purifying the recombinant Placental Growth Factor (PLGF) expressed in inducible prokaryotic expression systems comprising the following steps: I) fermentation of the bacterial cells, II) extraction and purification of the inclusion bodies, III) renaturation of the expressed protein, IV) ion-exchange chromatography, V) reverse-phase chromatography.

24 Claims, 5 Drawing Sheets

PRODUCTION PROCESS OF RECOMBINANT PLACENTAL GROWTH FACTOR

FIELD OF THE INVENTION

The present invention relates to a process for extracting and purifying the recombinant Placental Growth Factor from genetically modified cells.

STATE OF ART

The Placental Growth Factor (PLGF) is a homodimeric glycoprotein with a structure similar to the Vascular Endothelial Growth Factor (VEGF). The complete polynucleotide sequence codifying the PLGF protein was described by Maglione and Persico in patent EP-B-550 519 (WO-A-92/06194) claiming Italian priority of 27.09.1990. Alternative processes of splicing the ARN of PLGF generate three homologue forms of the Placental Growth Factor, precisely PLGF-1, PLGF-2 and PLGF-3, having different polypeptide sequences, and all described in literature.

The above-mentioned patent also describes a method for producing the PLGF factor comprising the use of an inducible prokaryotic expression system characterised by host cells modified with an expression vector, in which the human PLGF gene is integrated under the control of an inducible promoter (directly or indirectly). After inducing the PLGF expression with appropriate activator, the cells are incubated, isolated and submitted to lysis.

The so-obtained raw lysate is a complex mixture of proteins containing low quantities of the expressed PLGF protein and having low specific activity. In fact, in the known process, the protein expression is induced in cultures containing low cellular density, as it is evident from the low optical density at time of induction, that is between 0.2 and 0.6 OD at 600 nm. Furthermore, the process described in the preceding document does not comprise additional purification stages of the expressed protein. For this reason, the lysates obtained according to the application WO-A-92/06194 are inappropriate as such to be used directly in the preparation of medicaments.

A more complex method for purifying the same placental factor is envisaged by Maglione et al. in "Il Farmaco" 55 (2000), pages 165 to 167. Nevertheless, the method disclosure merely gives a simple listing of known applicable techniques, without describing conditions and experimental details thereof, which are essential for obtaining the PLGF protein in the purity and quantity necessary for a pharmaceutical use.

The scope of the present invention is to provide a new method for extracting and purifying the recombinant PLGF expressed in bacterial cells, allowing to obtain PLGF at high level of purity and with yields suitable to be industrially used in the preparation of medicaments.

A further scope of the invention is to obtain the PLGF protein in essentially active form (greater than 98.5%), that is mainly composed by dimeric (not less than 70%) and multimeric forms and containing residues of the monomeric form (little or not active) not greater than 1.5%.

SUMMARY OF THE INVENTION

The invention is based upon the identification of a sequence of purification techniques particularly appropriate for the extraction and purification of human PLGF expressed in bacterial cells. The invention is further based upon the determination of the optimum operative conditions with respect to the single techniques and to the chemical-physical features of the substance to be purified.

Then, object of the present invention is a process for extracting and purifying the recombinant Placental Growth Factor (PLGF) expressed by means of an inducible prokaryotic expression system comprising the steps of: I) fermentation of the bacterial cells, II) extraction and purification of the inclusion bodies, III) renaturation of the expressed protein, IV) ion-exchange chromatography, V) reverse-phase chromatography, and optionally VI) final stages of ultrafiltration, formulation and lyophilization. According to such method, the fermentation (step I) is performed until obtaining a high bacterial density in the medium, as it is shown by the high optical density in the medium, before proceeding with the induction step. The step (II) comprises bacterial lysis, rupture of DNA and isolation of the inclusion bodies. The renaturation of the expressed protein (step III) is obtained by solubilizing the inclusion bodies in denaturant buffer, and by transforming, at least partially, the expressed protein in the dimeric form. At last, in the step (IV) and (V) the dimeric and multimeric forms of the expressed protein are separated from the monomeric form and isolated in pure form, to be subsequently ultrafiltrated and lyophilised in presence of usual lyophilisation and formulation additives.

A specific object of the invention is the above-mentioned process for extracting and purifying the PLGF-1 protein of human origin, but substantially valid also for PLGF-1 of animal origin.

The claimed process advantageously allows the obtaining of production yields of expressed protein from 30 to 50 times higher than the yields obtained according to the method described in the preceding state of art. The claimed process furthermore allows the obtaining of the highly pure protein, with high specific activity and in substantially dimeric form.

Further object of the invention is the active Placental Growth Factor obtainable by means of the process of the invention, free from any residual protein or other bacterial contaminant and containing residues of monomeric form not higher than 1.5%.

DETAILED DESCRIPTION OF THE INVENTION

Figure 1:
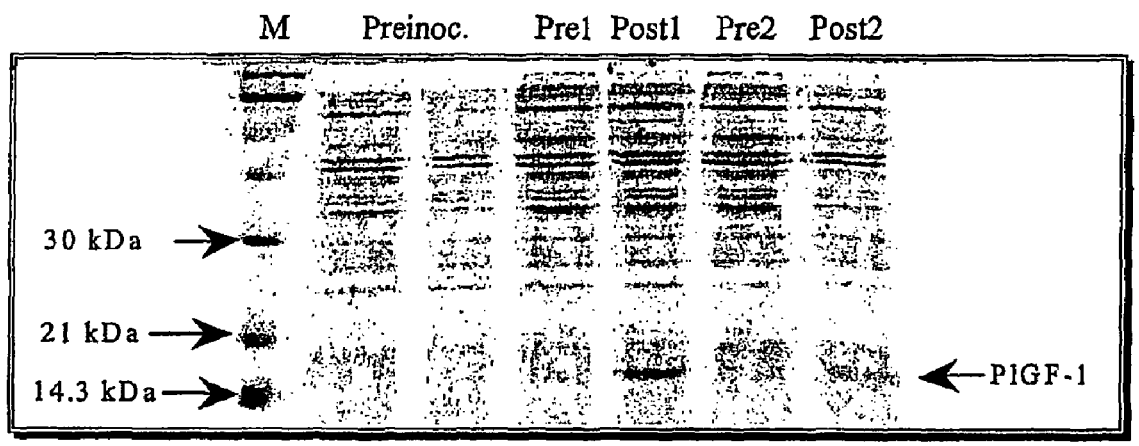
FIG. 1: The figure shows the results obtained by electrophoresis SDS-PAGE under reducing conditions for monitoring step I. Pre1 and Pre2 represent the pre-induction checks, prepared as follows. Soon before the induction, about 0,064 units of optical absorption measured at 600 nm (OD600) are taken and diluted 5 times with water. Of this dilution 20 µl are taken which are added to 20 µl of reducing buffer and submitted to boiling. 20 µl of this last solution are loaded onto the SDS PAGE matrix. Post1 and Post2 represent the post-induction checks prepared as above. M designates the mixture of markers of molecular weight. In the post-induction columns (Post1 and Post2) a band is noted just above the indicator of molecular weight 14.3 substantially absent in the pre-induction columns (Pre1 and Pre2) corresponding to the PLGF-1 protein expressed and segregated within the inclusion bodies.

The genetic modification of the bacterial host cells is described by Maglione et al. in the preceding patent EP-B-0550519 (WO-A-92/06194). For this purpose, bacterial cells are transformed introducing of an expression vector comprising an insert corresponding to the human gene coding for PLGF-1 factor. The complete gene sequence is known in literature and it is freely accessible. A plasmid containing such sequence was deposited with the ATCC under accession number ATCC No 40892. The expression is performed under the control of the system of RNA polymerase of T7 phage and it is induced with IPTG (isopropyl-β-D-tiogalactopyranoside).

Nevertheless, other inducible prokaryotic expression systems may be utilised. Examples of such systems, obtainable on the market, are represented by:

1) pBAD expression system (In vitrogen BV) wherein the synthesis of a protein is placed under the control of the araBAD promoter and it may be induced in different strains of $E.$ $Coli$ by means of arabinose.

2) T7 Expression System (In vitrogen BV or Promega) wherein the synthesis of a protein is controlled by the promoter of RNA polymerase of T7 phage and it may be induced by means of lactose or the analogues thereof (IPTG). In this case it is required the use of $E.$ $Coli$ derivatives of DE3 (Bl21(DE3) or JM109(DE3)) type containing, namely, a copy of the gene of Rna polymerase of T7 phage placed under the control of a lactose-inducible promoter.

3) Trc expression system (In vitrogen BV) wherein the synthesis of a protein is placed under the control of the trc hybrid promoter. Such promoter has been obtained by melting the trp promoter and the lac promoters and it may be induced in different strains of $E.$ $Coli$ by means of lactose or the analogues thereof (IPTG).

4) Tac expression system (Amerham biosciences) wherein the synthesis of a protein is placed under the control of the tac promoter. In this system the protein synthesis is induced in strains of $E.$ $Coli$ lacIq (type JM105) by means of lactose or the analogues thereof (IPTG).

5) $P_L$ expression system wherein the synthesis of a protein is placed under the control of the PL promoter and it may be induced by adding tryptophan. In this case it is required the use of $E.$ $Coli$ derivatives (GI724) containing a copy of the codifying gene for the cI repressor of the Lambda phage placed under the control of a tryptophan-inducible promoter.

Step I: Fermentation and Induction

The first stage of the claimed process consists in the fermentation of a functionally-modified bacterial strain equivalent to the strain described in the preceding European patent (above). In a preferred embodiment the micro-organism is a derivative of $Escherichia$ $Coli$ modified with an expression plasmid comprising the human gene of PLGF. A preferred micro-organism is the one called [B12(DE3)pLysS PLGF-1] obtained by integrating in the commercially available strain [B12(DE3)pLysS] (Promega Corporation USA) the gene of the human PLGF-1. The present invention, nevertheless, is not limited to the human PLGF-1 factor, but it also relates to the one of animal origin (monkey, mouse, rabbit etc.). The present invention is not limited so much the less to the use of a $E.$ $Coli$ derivative, but it includes the use of any prokaryotic micro-organism susceptible to be genetically modified and able to express heterologous proteins under the form of inclusion bodies.

The strains utilised as inoculum in the process of the invention are kept before using them in the lyophilised form to preserve the expression capacity thereof. Upon use, the lyophilised material is brought again in solution by utilising an appropriate buffer.

Although there is a wide range of known culture media available on the market and which may be effectively used, the fermentation step according to the invention is preferably performed in a medium free from any material of animal or human origin in order to avoid any infection risk. Yeast's extracts (Difco) added with one or more suitable antibiotics represent the most suitable means for the process. In the preferred embodiment a medium is used which has been obtained by mixing under sterility conditions a first solution (A) containing yeast's extracts, glycerol and ammonium sulphate with a second solution (B) containing a phosphate buffer. The mixture is then integrated with ampicillin and chloramphenicol or equivalent antibiotics. Appropriate antibiotic concentrations are from 50 to 300 µg/ml of ampicillin, preferably from 100 to 200 µg/ml and from 10 to 100 µg/ml of chloramphenicol, preferably from 30 to 40 µg/ml.

The fermentation step may be preceded by a preinoculum step wherein the lyophilised micro-organism is suspended in the medium and submitted to consecutive incubation and dilution steps aimed at having in culture the optimum quantity of micro-organism cells. Preferably, the micro-organism is incubated for one night at 37° C., then diluted and incubated again for some hours. The chosen pre-inoculum volume is subsequently centrifuged, suspended again in the culture solution enriched with ampicillin and inoculated in the fermentation vessel for the fermentation step.

The fermentation is performed in the above-mentioned medium added with ampicillin and chloramphenicol at the temperature suitable for the micro-organism, usually at about 37° C., in presence of a percentage of dissolved O2, with respect to the saturation with air, from 20% to 40%, preferably 30%. The pH during fermentation is kept at neutral or weakly acid values (6.4 to 7.4). Furthermore, since the fermentation process takes place under stirring, antifoam agents are preferably to be used.

The fermentation progress is accompanied by the increase in the optical density of the medium. For this reason, the optical density is the parameter utilised according to the invention to monitor the progress degree of the fermentation. Readings at 600 nm are particularly appropriate.

Essential feature of the invention is the high cellular density achieved in the culture at time of the expression induction. Optical densities at 600 nm (OD600) from 1 to 50 may be achieved thanks to culture media of the invention. Densities higher than 18, nevertheless, are preferred to obtain the high production levels typical of the claimed method. Densities between 16 and 20 are particularly preferred to induce the producing bacterial strain and gave optimum results. The fermentation, then, is kept at the above-mentioned conditions until achieving such values of optical density, then one proceeds to induce the protein expression.

Any agent or chemical-physical condition able to induce in the cells of the used micro-organism the machinery of expression of the heterologous protein may be advantageously utilised. In the specific case wherein the bacterial strain BL21 (DE3)pLysS modified with an expression plasmid containing the promoter of T7 phage is used, the expression is induced with lactose or the derivatives thereof, such as isopropyl-β-tiogalactopyranoside (IPTG) with a proper concentration, namely about 1 mM. The induction duration may vary according to need. Good results are obtained for periods of some hours, preferably from 3 to 4 hours; in the optimum process the induction is kept for 3 hours and 20 minutes by using a percentage of dissolved O2 equal to about 10%.

Cell samples are taken before and after induction and submitted to analytical techniques of control such as electrophoresis on SDS-PAGE, to determine the induction outcome.

When the protein expression reaches the desired levels, the culture is centrifuged and the cells are moved to the following step.

Step II: Extraction and Purification.

The expressed heterologous protein in bacterial strains is segregated inside the cell itself in the form of inclusion bodies. Therefore, the process of the invention provides passages of lysis of the cells, rupture of the extracted nucleic material (DNA) and recovery and washing of the inclusion bodies.

The cells are washed, although not necessarily, and suspended in solutions containing emulsifier agents in appropriate concentration, preferably Triton X100 in concentrations from 0.5% to 1%, then they are submitted to lysis of the cellular membrane. The lysis process may be performed by means of freezing/thawing, French Press, sonication or other similar known techniques. Nevertheless, the preferred method for the bacterial strain BL21(DE3)pLysS is the freezing/thawing method, which in the most preferred embodiment is repeated at least for two consecutive cycles. After the mechanical lysis, the lysis stage is continued for a few minutes in the lysis solution at room temperature under stirring.

The release in the lysis medium of the inclusion bodies is accompanied by the release of micro-organism different components and cellular substances, above all the nucleic materials. These substances could interfere with and jeopardise the following protein purification process. Therefore, the suspension/solution obtained by lysis is submitted to rupture of such nucleic material, specifically DNA, by means of enzymatic agents, such as DNAse (natural or recombinant such as the Benzonase), chemical agents, such as deoxycholic acid, or physical-mechanical agents, such as sonication or high energy stirring by means of blades, for example, in a mixer. The rupture of DNA, carried out for example in a mixer, is performed on lysed cells re-suspended in appropriate volumes of washing solutions containing chelating and detergeing agents, for example EDTA and Triton X100. It is preferably repeated for more cycles, preferably 2, alternated with stages of dilution, in washing solution, centrifugation and elimination of the supernatant in order to remove components and cellular substances from the fraction containing the inclusion bodies.

Step III Renaturation (Refolding) of the Protein

Figure 5:
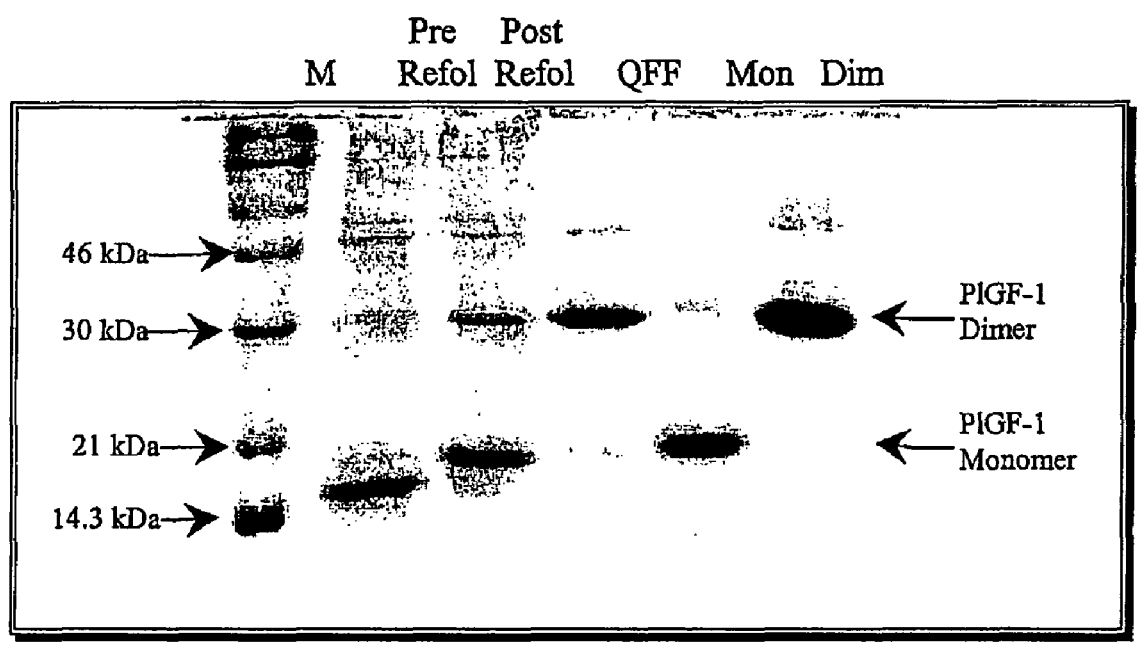
FIG. 5: The figure shows the results obtained in electrophoresis on SDS-PAGE for the final monitoring of the whole process. Prerefol and Postrefol represent the checks preceding and following the renaturation of the expressed protein (step III). QFF represents the peak eluted from the Q Sepharose fast flow resin, containing the protein mainly in dimeric form. Mon represents the peak containing the monomeric form. Dim represents the peak eluted in the second substep of the reverse-phase chromatography on RP Source 30 resin. It is noted that before the renaturation, the expressed protein is mainly in monomeric form. After the renaturation, part of the protein is in dimeric form. The following purification on QFF and RF 30 chromatography allow the obtaining of PLGF-1 protein with high purity degree.

The fraction containing the purified inclusion bodies of PLGF-1 is then solubilised in denaturing buffer containing known denaturant agents such as urea, guanidine isothiocyanate, guanidine-hydrochloride. Preferably, the denaturant solution is a urea solution in denaturant concentration, for example 8M. In order to accelerate the solubilisation process, the fraction may advantageous be submitted to homogenisation or sonication. After solubilizing the inclusion bodies, the solution is diluted with the same denaturant buffer until obtaining an optical density measured at 280 nm of about 0.8 (OD280 0.8). Subsequently, the solution is further diluted with a dilution buffer until 0.5 OD280. Suitable dilution solutions contain salts and polyethylene glycol (PEG) and have basic pH (about 8). The renaturation of the PLGF-1 protein in diluted solution is obtained by adding to the solution appropriate concentrations of oxidising/reducing pairs, followed by an incubation of 10 to 30 hours, preferably 18 to 20 at a temperature of 10° C. to 30° C., preferably 20° C., under stirring. Examples of such pairs are: Cystine/Cysteine, Cystamine/Cysteamine, 2-hydroxyethyldisulphide/2-mercaptoethanol. Preferred example of oxidising/reducing pair is the glutathione in its oxidised and reduced forms, respectively at concentrations between 0.1 mM and 2.5 mM (preferably 0.5 mM) and between 0.25 mM and 6.25 mM (preferably 1.25 mM). By means of renaturation, the PLGF-1 protein expressed essentially in monomeric form is partially brought back to the dimeric form (FIG. 5).

Step IV: Anionic-exchange Chromatography

The solution coming from the preceding step, preferably through centrifugation and/or filtration and containing the protein in mainly monomeric and partially dimeric form, is loaded onto anion-exchange resin in order to enrich the mixture with the dimeric form and to purify it from bacterial contaminants. Any commercially available matrix suitable for anion-exchange chromatography may be likewise used to the extent that its features of capacity, loading and flow speed be similar to those of the Q Sepharose Fast Flow resin (Amersham biosciences), apart from being suitable for an industrial process. In a preferred embodiment a high-flow resin is used, for example Q-sepharose Fast Flow (Amersham biosciences) or equivalent. The resin is washed and equilibrated with solutions having low ionic strength. An example of such solution comprises ethanolamine-HCl pH 8.5 with low or absent salt content. The same solution may be utilised for loading, absorbing and washing the protein mixture to be purified. The used resins allow loading of large volumes of protein solution with ratios Volume loaded/Volume column varying from 1:1 to 10:1. Ratios Vol./Vol. next to 10:1 are preferred since they allow optimising the use of the column. However, ratios higher than 10:1 are to be avoided since, due to the saturation of the adsorbing capacity of the matrix, they lead to high loss in the dimeric form of the protein.

Figure 2:
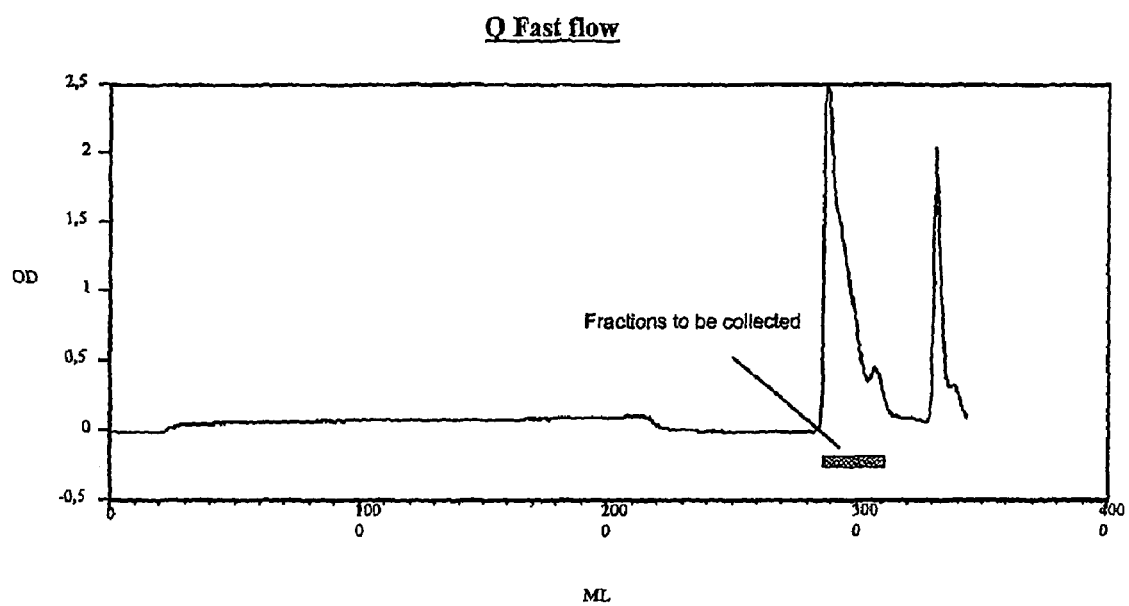
FIG. 2: The figure shows the monitoring chromatogram of the anionic-exchange chromatography on Q-Sepharose Fast Flow resin. X-axis shows the elution volume (ML), y-axis shows the optical absorption units (OD). The first elution peak obtained by eluting by 20% with buffer B (NaCl 200 mM) corresponds to the PLGF-1 protein in substantially dimeric form, but it comprises impurities and the monomeric form. The following peak, eluted by 100% with buffer B (NaCl 1M) contains impurities which are eliminated.

Whereas the PLGF-1 protein in monomeric form already percolates in the stages of washing with low ionic strength, the elution of the dimeric and multimeric forms is obtained by increasing the ionic strength of the starting solution. Such increase is obtained by mixing the equilibration solution with increasing and pre-established percentages of a second solution containing NaCl 1M. In a preferred embodiment, the protein in dimeric form is eluted with solutions containing from 15% to 25% of NaCl 1 M solution, which corresponds to a NaCl concentration from 150 to 250 mM. In the best embodiment, the protein is eluted in isochratic conditions at NaCl concentration of 200 mM. The elution of the various species is automatically monitored by measuring the optical absorption at 280 nm (FIG. 2). The collected fractions containing the PLGF-1 protein in dimeric form are subsequently controlled by electrophoresis SDS-PAGE (FIG. 5). Advantageously, the whole chromatography process is automatically performed by a computerised system operating under the control of a suitable programme, for example the Software FPCL Director system (Amersham biosciences).

Step V: Reverse-phase Chromatography

The fractions coming from the preceding step containing the PLGF-1 protein enriched with the active forms are collected, diluted with appropriate buffer and loaded onto an reverse-phase chromatography column in order to further purify the protein in active form. The quantity of loaded solution corresponds to OD280 between 4.5 and 5.5 per millilitre of chromatographic matrix. Such quantities are to be considered maximum quantities.

Any commercially available chromatographic matrix suitable for the intended use may be utilised to the extent that its features of loading capacity and flow speed are compatible with the process requirements. In a preferred embodiment, a resin is used having such bead-sizes so as to guarantee the best exploitation of the absorbing capability together with the easiness in packing the column itself. Examples of such matrixes are the RP Source 15 or RP Source 30 (Amersham biosciences) resins. All the solutions for equilibration, loading, resin washing and elution are hydro-organic solutions comprising different percentages of organic solvent. Examples of such solutions are solutions comprising ethanol, methanol or acetonitrile. Preferably, hydro-alcoholic solutions comprising increasing percentages of ethanol are utilised. In an embodiment of the invention appropriate quantities of two buffer solutions are mixed, the former comprising buffer A, i.e. ethanol 40% and TFA (trifluoroacetic acid) 0.1%, the latter comprising buffer B, i.e. ethanol 70% and TFA 0.1%.

Figure 3:
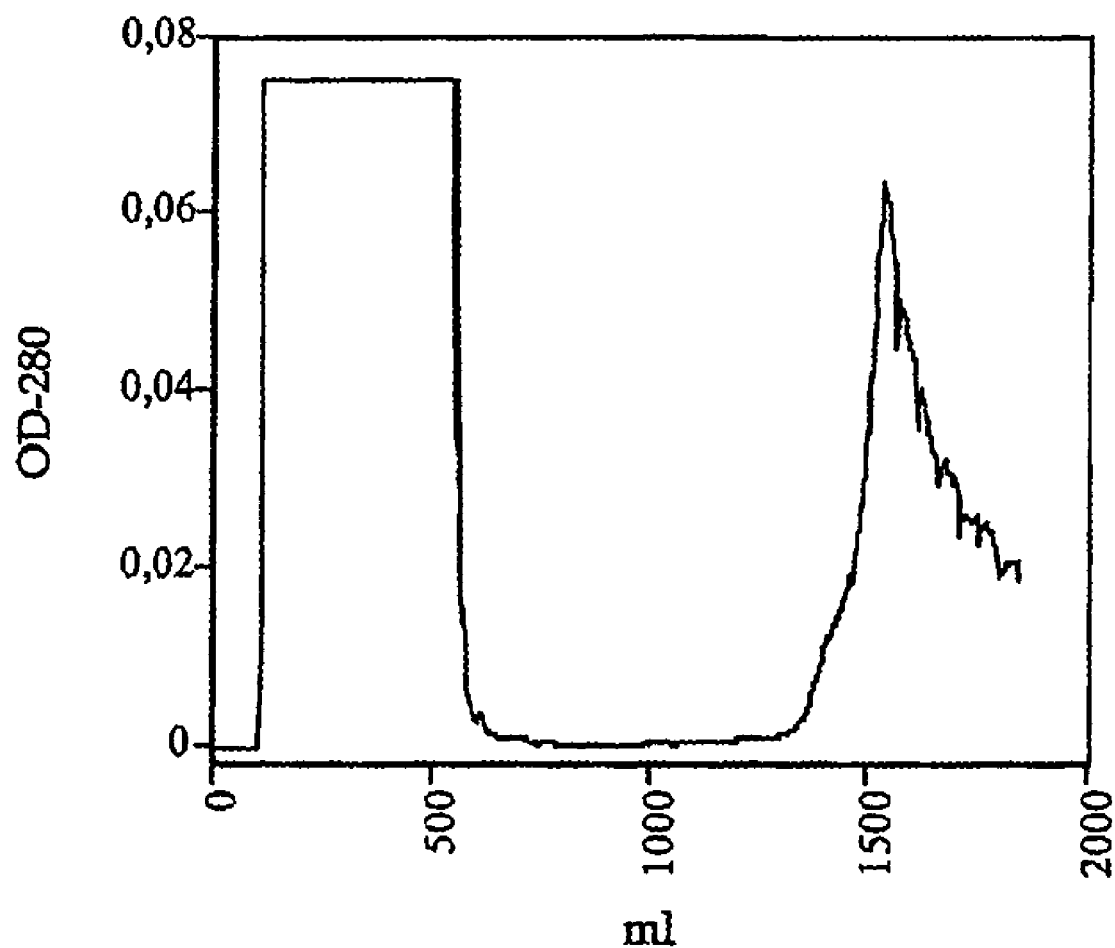
FIG. 3: The figure shows the monitoring chromatogram of the first elution stage in reverse-phase chromatography on RP Source 30 resin. X-axis shows the elution volume (ml), y-axis shows the optical absorption units (OD). The first abundant elution peak corresponds to the various impurities, which do not bond to the resin. The second elution peak corresponds to the PLGF protein in monomeric form eluted under isochratic conditions (experimentally found at about 10%-15% of buffer B).
Figure 4:
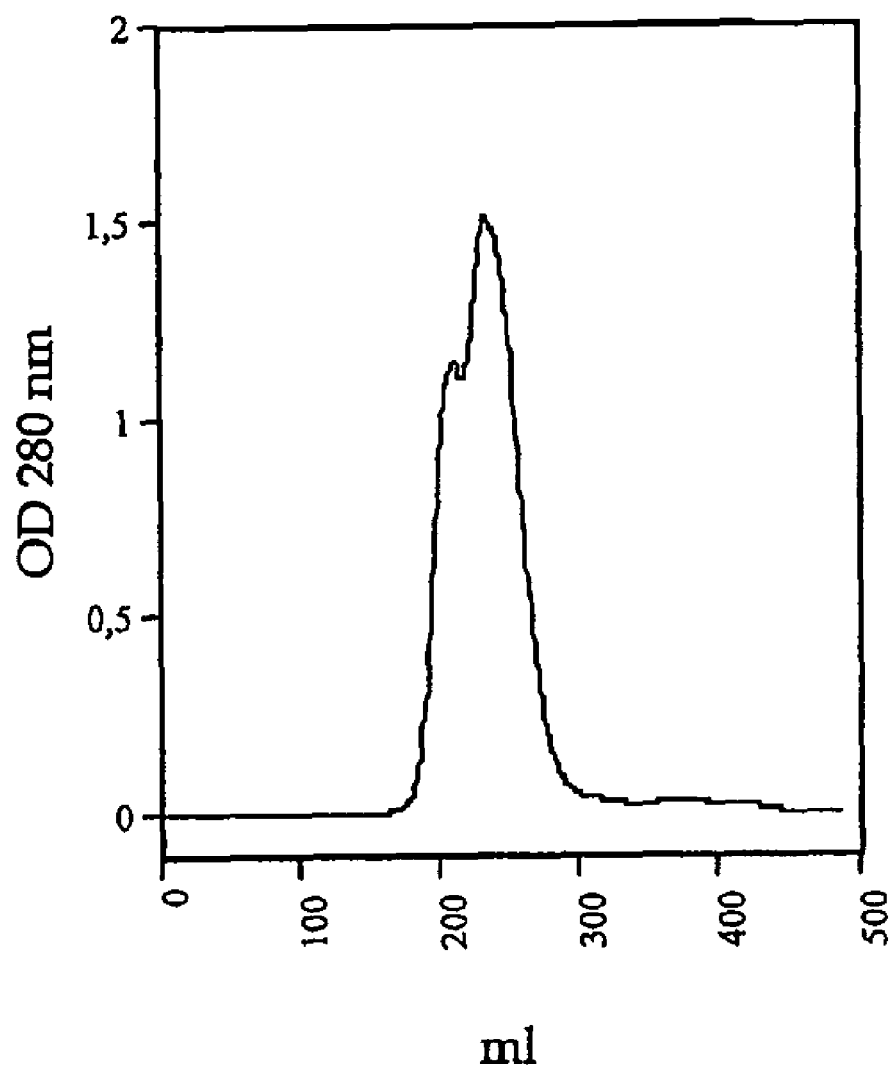
FIG. 4: The figure shows the monitoring chromatogram of the second elution stage in reverse-phase chromatography on RP Source 30 resin. X-axis shows the elution volume (ml), y-axis Shows the optical absorption units (OD). The elution peak corresponds to the PLGF protein in dimeric-multimeric form.

The protein material loaded onto the resin and properly washed is then eluted through an elution process comprising two subsequent stages wherein elution solutions containing an increasing gradient of organic solvent are utilised. The first stage is performed under conditions of rising gradient of organic solvent until obtaining the elution peak of the monomeric form. Such gradient is obtained by adding the buffer B to the buffer A in percentages from 4% to 40%, with an increasing rate of buffer B of 3% for each eluted column volume. As soon as the elution peak corresponding to the monomeric form of the protein appears, the elution is continued under isochratic conditions until exhaustion of the elution peak of the monomeric form. The so-set isochratic conditions cause the largest possible separation of the chromatographic peaks corresponding to the two monomeric and dimeric forms and, then, the best obtainable resolution for a process of industrial, and not analytical type. The second stage is performed again under condition of increasing gradient of organic solvent until whole elution of the protein mainly in dimeric form is achieved. In this second stage, the gradient is obtained by adding the buffer B to the buffer A in percentages from 10% to 100%, with an increasing rate of buffer B of 40.9% for each eluted column volume. The elution of the various forms of PLGF-1 protein is automatically monitored by measuring the optical absorption at 280 nm (FIG. 3 and FIG. 4). The collected fractions containing the PLGF-1 protein essentially in dimeric form are subsequently controlled by electrophoresis SDS-PAGE (FIG. 5). Advantageously, the whole reverse-phase chromatography process is automatically performed by a computerised system operating under the control of a suitable programme, for example the Software FPCL Director system (Amersham biosciences).

The results of the electrophoresis show that PLGF-1 protein obtained from the second stage of the reverse-phase chromatography is in highly pure active form, namely it comprises the protein in dimeric and partially multimeric form, but it is essentially free from any contamination of the monomeric form. The so-obtained product comprises not less than 98.5% of active form, preferably not less than 99.5%, wherein not less than 70% is in dimeric form. The residual of monomeric form is not higher than 1.5%. The protein in active form is obtained in average amounts of 160 mg per litre of bacterial culture. The pure protein obtained according to the above-described method may be submitted to additional working stages such as ultrafiltration on membrane. In this case the product is filtered on membrane having cut-off limit lower than, or equal to 30 kD and it is submitted to diafiltration against TFA acidulated water until a dilution factor of 1:106. The so-obtained final product may be properly formulated with lyophilisation additives and lyophilised to keep its best biological activity.

The invention is here below described by means of examples having, however, only illustrating and not limiting purposes.

EXAMPLE 1

Fermentation

The following procedure relates to the method of fermentation and induction of the genetically modified micro-organism (MOGM) [Bl21(DE3)pLysS PlGF-1] in a fermentation vessel using 1 mM IPTG.

| Materials: | |
|---|---|
| Solution SBM constituted by: Solution A (per 1 liter) | |
| Bacto yeast extract (Difco) | 34 g |
| Ammonium sulphate | 2.5 g |
| Glycerol | 100 ml |
| H2O q.s. at: | 900 ml |
| Solution B (10 X) (per 100 ml) | |
| KH2PO4 | 1.7 g |
| K2HPO4 –3H2O | 20 g, or |
| K2HPO4 | 15.26 g |
| H2O q.s. at | 100 ml |

The solutions A and B are separately autoclaved and mixed upon use under sterile conditions. Alternatively, the solutions A and B are mixed and filtered under sterile conditions.

IPTG 200 mM (200X) is produced by dissolving 5 g of pure substance in 100 ml of distilled water. The solution is filtered by means of 0.22-μm filters, subdivided into aliquots and frozen at −20° C.

The utilised antifoam agent is Antifoam O-10 (not siliconic) Sigma Cat A-8207.

The used bacterial strain is [BL21pLysS PlGF-1 WCB] (working cell bank).

Preinoculum: A tube of lyophilised genetically modified micro-organism (MOGM) WCB is taken and it is suspended in 1 ml of SBM+100 μg/ml Ampicillin+34 μg/ml of chloramphenicol.

The suspension is diluted in 30 ml of SBM+100 µg/ml Ampicillin+34 pg/ml of chloramphenicol.

The suspension is incubated at 37° C. for one night (O/N). The day after the 30 ml of the O/N culture are diluted in 800 ml of SBM+100 pg/ml Ampicillin+34 µg/ml of chloramphenicol and they are subdivided into 4 1-liter Erlenmeyer flasks, each containing 200 ml.

The content of each flask is incubated at 37° C. for 24 hours. The content of the 4 flasks is mixed and the OD600 are read by diluting 1/20 in water (50 µl+950 µl of water).

An established volume of preinoculum is then centrifuged for 10 min. at 7.500×g at 4° C. in sterile tubes.

The bacteria are then re-suspended in 20 ml of SBM+200 µg/ml of Ampicillin+10 µg/ml chloramphenicol per each litre of fermentation by stirring at 420 rpm at R.T. for 20 minutes. At the same time the fermentation vessel is prepared and the oxygen probes are calibrated.

The oxygen probes are calibrated at 37° C. temperature at 0% with nitrogen, then at 100% with air without antifoam under stirring at 600 RPM.

The fermentation is carried out under the following experimental conditions:

Medium: SBM+200 ug/ml of ampicillin and 10 µg/ml of chloramphenicol

| Temperature: | 37° C. |
|---|---|
| % dissolved O2: | 30% (with respect to saturation with air) |
| pH: | from 6.4 to 7.4. |

Antifoam: 1:10 is diluted in water; strongly stirring before adding it in quantities of 140 µl per 750 ml of medium.

Induction:

The induction is carried out under the following experimental conditions:

| OD600 of induction: | 16–20. |
|---|---|
| Inducing agent: | IPTG 1 mM final. |
| % dissolved O2: | 10% (with respect to saturation with air). |
| Induction length: | 3 hours and 20 minutes. |

Just before the induction 20 µl of bacteria are taken, added to 80 µl of water and kept for the pre-induction check.

At time of induction, IPTG is added to the final concentration of 1 mM.

The percentage of dissolved O2 is brought to 10%.

At the end of the induction the final OD600 are read and the overall volume is measured.

Then, 10 µl of bacteria are taken, added to 90 µl of water and kept for the post-induction check.

The induction is controlled by way of a SDS-PAGE electrophoresis by loading 20 µl of the 2 previously boiled samples.

The medium containing the induced bacteria is then centrifuged at 7.500×g for 10 min. or at 3000×g for 25 min. at 4° C. and the supernatant is eliminated.

Results: The induction results are checked by SDS-PAGE electrophoresis as shown in FIG. 1.

EXAMPLE 2

Extraction and Purification of the Inclusion Bodies

The following procedure relates to the preparation and refolding of the inclusion bodies of PlGF-1. By means of refolding the PLGF-1 bacterial protein is partially brought back to the dimeric form.

Material:
Mixer with appropriate capacity.

| Lysis solution: | 1 mM Mg2SO4 + 20 mM Tris-HCl pH8 + Triton X100 by 1%. |
|---|---|
| Washing solution: | 0.5% triton X100 + 10 mM EDTA pH 8. |
| BD (denaturing buffer): | 8 M urea, 50 mM Tris pH 8, Ethylenediamine 20 mM. |
| | Dissolving and bringing to volume in H2O. |
| Oxidised glutathione 200x: | 100 mM in H2O; |
| Reduced glutathione 200x: | 250 mM in H2O. |
| Dilution buffer: | 600 µM final PEG 4000 (2.4 g/l), 50 mM Tris-HCl pH 8, 20 mM NaCl. |
| Antifoam: | Antifoam O-10 (not siliconic) Sigma. |

Preparation of the PLGF-1 Inclusion Bodies.

The lysis and washing solutions are equilibrated at room temperature (RT).

Two cycles of freezing/thawing at −80/37° C. are performed.

The bacterial pellet is lysed in 1 ml of lysis solution per each 450 OD600 of bacteria.

It is then incubated at RT 30 min. under stirring (250 RPM).

The solution is poured into a mixer with appropriate capacity and a quantity of washing solution of 3 ml for each 450 OD600 of bacteria is added.

If necessary, 0.4 µl of not-diluted antifoam per each millilitre of sample are added.

The solution is spun at the maximum speed for 1 minute or until the sample is well homogeneous.

The content of the mixer is then transferred into a container with appropriate capacity and,6,5 ml of washing solution per each 450 OD600 of bacteria are added. It is incubated for 45 min. at RT under stirring.

The so-obtained suspension is centrifuged at 13.000×g for 45 min. at 25° C. and the supernatant is discharged.

The settled pellet is re-suspended in 4 ml of washing solution per each 450 OD600 of bacteria and the cycle in the mixer is repeated for the second time.

The suspension is transferred into a container with appropriate capacity, diluted with 6.5 ml of washing solution per each 450 OD600 and incubated for 30 min. at RT under stirring.

The centrifugation under the above seen conditions is then repeated and the supernatant is eliminated.

EXAMPLE 3

Renaturation of the Protein

The inclusion bodies are solubilised in 7 ml of denaturing buffer BD (containing urea 8M) and further diluted in BD until OD280 of 0.8. Subsequently, 0.6 volumes of dilution buffer are added in order to bring the final urea concentration to 5M.

Afterwards 1/200 of reduced glutathione 200× (final concentration of 1,25 mM) and 1/200 of oxidised glutathione 200× (final concentration of 0.5 mM) are added. A 15 µl sample for checking (prerefol) is taken and the solution is then incubated at 20° C. for 18-20 hours under stirring.

At the end of the incubation, the medium is centrifuged for 10 min. at 20° C., 10.000×g, filtered by means of 0.45 or 0.8 μm filters and a 15 μl sample is taken for checking (postrefol).

Results: The 15-μl samples of the pre- and post-refolding solutions are analysed by means of SDS-PAGE electrophoresis (FIG. 5).

EXAMPLE 4

Anion-exchange Chromatography

The following procedure relates to the first step of purification of the PlGF-1 protein after refolding. Upon loading of the sample onto the column, there will be a high loss of not-absorbed PlGF-1 monomer. The loaded quantity must not exceed 10 times the volumes of the column, since this would cause a significant loss in the PLGF-1 dimer.

The elution is performed under isochratic conditions at 20% of buffer B (see below), which corresponds to a NaCl concentration of 200 mM. The eluted peak still contains the glutathiones used for refolding, which contribute by about 50% of OD280.

Material and parameters:

| | |
|---|---|
| FPLC system: | Amersham-biosciences handled by the software called FPLC Director. |
| | Monitoring parameters |
| U.V.: | Wavelength = 280 nm; scale top = 2. |
| Temperature: | 20° C. (minimum 15, maximum 25) |
| Resin: | Q-sepharose Fast Flow (Amersham-biosciences) |
| Column volume/height: | Volume: 1/10 of volume of the sample to be loaded; height: between 13 and 16 cm. |
| Equilibration: | 2 Column Volume (CV) of buffer B, then 1.5 CV of buffer A. |
| Sample: | Renatured, centrifuged and/or filtrated P1GF-1. Load no more than 10 CV thereof. |
| Buffer A: | 20 mM Ethanolamine-HCl pH 8.5. |
| Buffer B: | Buffer A + 1M NaCl. |
| Injection speed: | 1 cm/min (maximum speed tested on small columns = 1.887 cm/min; minimum tested speed = 0.5 cm/min.). |
| Elution speed: | 1 cm/min (maximum speed tested on small columns = 1.887 cm/min; minimum tested speed = 0.5 cm/min.). |
| Washings after Injection: | 1.5 CV with 0% of buffer B. |
| Peak collected: | Peak eluted at isochratic conditions at 20% of buffer B, running for about 3 CV. |
| Final washing: | 2 CV at 100% B. |

Procedure:

The peak eluted under isochratic conditions at 20% of buffer B is collected, then 0.271 water volumes, 0.0045 TFA volumes and 0.225 ethanol volumes are added thereto. In this way the sample results to be diluted 1.5 times and contains 15% ethanol and 0.3% TFA. The addition of these 2 substances facilitates the bounding of PlGF-1 to the reverse-phase resin (see example 5).

Results: The chromatography step is continuously controlled by monitoring the optical densities at 280 nm as illustrated by FIG. 2.

The purity of the isolated protein material is analysed by means of SDS-PAGE electrophoresis (FIG. 5).

EXAMPLE 5

Reverse-phase Chromatography

The following procedure may be performed with RP source resin with 15 micron or 30 micron average particle diameter. However, the 30-micron RP source resin, while not involving any alteration in the purification process, allows an economical saving of the resin itself (about 50%), a greater easiness in the packaging procedure of the column and a lower backpressure.

The procedure relates to the second phase of the purification of the PlGF-1 protein after passing on the QFF resin. During the sample injection, a high adsorbance is apparent and corresponds to the not adsorbed peak of the glutathiones which do,not bound to the resin. This procedure consists of 2 sub-stages, the, former called RPCmon, is used to eliminate most of the monomeric component of PlGF-1, whereas the latter is used to elute the essentially dimeric component of the protein and it is called RPCdim.

First Sub-stage (RPCmon)
Material and Parameters:

| | |
|---|---|
| FPLC system: | Amersham-biosciences handled by the software called FPLC Director. |
| | Monitoring parameters |
| U.V.: | Wavelength = 280 nm; full scale = 0.05. |
| Temperature: | 20° C. (minimum 15, maximum 25) |
| Resin: | Reverse Phase Source 30 (Amersham-biosciences). |
| Resin volume/height: | Volume: 1/3-1/5 of the overall OD280 of the sample to be loaded; height: between 27 and 33 cm. |
| Equilibration: | 2 Column Volume (CV) of buffer B, then 2 CV of buffer A. |

Sample: PlGF-1 coming from the preceding step (example 4), diluted 1.5 times and containing ethanol 15% and TFA 0.3%. Loading max. 4.5 to 5.5 OD280 per ml of resin.

| | |
|---|---|
| Buffer A: | Ethanol 40% + TFA 0.1%. |
| Buffer B: | Ethanol 70% + TFA 0.1%. |
| Injection speed: | 1.887 cm/min. |
| Elution speed: | 1.887 cm/min. |
| Washings after injection: | 1.5 CV with 4% buffer B. |

Monomer peak: Gradient ranging from 4 to 40% of B in 12 CV (3%B/CV). Just after starting the elution of the peak, by OD280 reaching 25% of the full scale, the elution is continued with isochratic conditions with the buffer B concentration reached in that moment until the peak elution is complete (about 2.5 -3.5 CV).

Operations

A suitable quantity of the solution corresponding to the "monomer" peak is taken and it is concentrated for checking (mon in FIG. 5).

Second Sub-stage (RPCdim)
Material and Parameters:

Without re-equilibrating the column, but by simply shifting the scale range of the UV monitor to the value 2, a gradient ranging from 10 to 100% of the buffer B is run in 2.2 CV (40.9%B/CV).

Operations:

The fractions corresponding to the "Dimer" peak are taken. FIG. 4 illustrates an example thereof. They are collected and the volume and the optical density at 280 nm are measured.

The overall yield (expressed in mg) obtained before the lyophilisation is calculated by multiplying the OD280 times the volume times the dilution. The average value of such yield is 164 mg of pure PLGF-1 per litre of bacterial culture with a standard deviation of 23.21. It may also be expressed in mg per 1000 OD600 of fermented bacteria, resulting to 5.58 mg of pure PLGF-1 each 1000 OD600 of fermented bacteria with a standard deviation of 0.8.

The so-obtained dimer solution is kept at $-20°$ C. until ultradiafiltration and lyophilisation. A sample of such solution is submitted to SDS-PAGE electrophoresis as illustrated in FIG. 5.

What is claimed is:

1. A process for extracting and purifying recombinant Placental Growth Factor (PLGF) protein in dimeric and multimeric active form containing no more than 1.5% of monomeric form, by expression of the PLGF protein in *E. Coli* cells modified with an inducible expression system comprising an insert coding for the PLGF protein, the process comprising in the following order:
   I) inoculating in a culture medium the *E. Coli* cells and fermenting the *E. Coli* cells until obtaining optical density of the culture medium from 14 to 50 at 600 nm ($OD^{600}$ 14-50);
   II) inducing the expression of PLGF protein via the inducible expression system;
   III) extracting the inclusion bodies by lysing the cultured cells, rupturing DNA of the cultured cells, isolating and purifying the inclusion bodies;
   IV) solubilizing the inclusion bodies into a denaturing buffer to form a solution and renaturating the expressed protein PLGF by adding to the solution oxidizing/reducing agents to bring the expressed protein to a dimeric form, at least partially;
   V) passing the solubilized protein on a high flow resin for anion exchange chromatography separating and isolating the dimeric and multimeric forms of the expressed protein from the monomeric form; and
   VI) further separating and finally isolating the dimeric and multimeric forms of the expressed protein from the monomeric form by passing them through a reverse-phase chromatography resin with two subsequent elution stages with increasing gradient of an organic solvent separated by an elution stage under isochratic conditions, wherein the organic solvent comprises ethanol, methanol, or acetonitrile, and wherein the monomeric form comprises no more than 1.5% of the total PLGF protein.

2. The process according to claim 1, wherein the Placental Growth Factor (PLGF) is human PLGF-1 or of non-human origin.

3. The process according to claim 1, comprising performing the fermentation in a medium comprising at least one selection agents, yeast extract, glycerol and ammonium salts.

4. The process according to claim 1, wherein the inducible expression system is a T7 RNA polymerase IPTG inducible system.

5. The process according to claim 4, comprising inducing the expression by adding a compound selected from the group consisting of lactose, isopropyl-beta.-D-thiogalactopyranoside (IPTG) and functionally equivalent analogues.

6. The process according to claim 1, wherein the bacterial strain is *E. Coli* {B121(DE3)pLysS}.

7. The process according to claim 1, comprising inducing expression when the optical density of the culture is 14 to 30 OD at 600 nm (14-30 $OD^{600}$).

8. The process according to claim 1, comprising performing the cell lysis by one of the group consisting of freezing/thawing and French press.

9. The process according to claim 1, comprising performing the DNA rupture by one of the group consisting of DNAse of extraction origin, DNAase of recombinant origin, and chemical-mechanical action.

10. The process according to claim 1, comprising performing the DNA rupture by mixing with a mixer.

11. The process according to claim 1, comprising isolating the inclusion bodies by centrifuging for at least two cycles and washing into a suitable buffer.

12. The process according to claim 1, wherein the extracting step further comprises homogenizing or sonicating the solution of inclusion bodies, and wherein the denaturing buffer comprising a compound selected from the group consisting of urea, guanidine isothiocyanate, and guanidine-hydrochloride.

13. The process according to claim 1, wherein in the renaturing step IV, the solution of the denatured inclusion bodies is incubated with the oxidising/reducing agents for 10 to 30 hours at a temperature of 10° C. to 30° C.

14. The process according to claim 13, further comprising diluting the solution of denatured inclusion bodies until obtaining an optical density at 280 nm ($OD^{280}$) from 0.01 to 2 and adding reduced/oxidised glutathione to form the dimeric form of PLGF protein.

15. The process according to claim 1, wherein, in step V, said passing is done with a ratio Volume loaded/Volume column from 1:1 to 10:1.

16. The process according to claim 15 wherein the ratio Volume loaded/Volume column is 10:1.

17. The process according to claim 15, comprising eluting the protein with an ethanolamine-HCl, NaCl elution buffer, wherein the protein in monomeric form is mainly comprised in the a percolate not bound to the resin of the anionic-exchange column, and wherein the protein in essentially dimeric form is eluted with elution buffers comprising NaCl at a concentration from 150 to 250 mM.

18. The process according to claim 17, comprising diluting the eluted fraction in essentially dimeric form and loading the eluted fraction of the protein in essentially dimeric form onto a reverse-phase chromatography column in an amount corresponding to an optical density from 4.5 to 5.5 OD at 280 nm per ml of resin.

19. The process according to claim 18, additionally comprising performing with first and second elution buffers a first elution stage under conditions of increasing gradient of organic solvent until the elution peak of the monomeric form appears, prosecuting the elution under isochratic conditions until exhaustion of the elution peak of the monomeric form, and performing a second elution stage under conditions of increasing gradient of organic solvent until complete elution of the protein in mainly dimeric form.

20. The process according to claim 19, wherein the first and the second elution buffers comprise a solvent selected from the group consisting of ethanol, methanol, and acetonitrile.

21. The process according to claim 19, wherein the first and the second elution buffers are a hydroalcoholic solution comprising increasing percentages of ethanol.

22. The process according to claim 18 comprising performing the reverse-phase chromatography on resin having particles with an average diameter of 30-micron.

23. The process according to claim 1, comprising performing after step IV an additional ultrafiltration step followed by lyophilisation.

24. A product obtained by the process of claim 1, the product comprising not less than 98.5% of Placental Growth Factor (PLGF) in active dimeric and multimeric form, the monomeric form in a percentage not higher than 1.5%, the product being free from bacterial contaminants.

* * * * *